(12) United States Patent
O'Lenick, Jr. et al.

(10) Patent No.: US 8,263,061 B2
(45) Date of Patent: Sep. 11, 2012

(54) ALKYL QUATERNIUM SILICONE COMPOUNDS

(75) Inventors: Anthony J. O'Lenick, Jr., Dacula, GA (US); Zhi Lu, Phillipsburg, NJ (US); Marian N. Holerca, Somerset, NJ (US); Mark Riddle, Toronto (CA); Gregory Szewczyk, Flemington, NJ (US); Rick Vrckovnik, Toronto (CA)

(73) Assignees: Colgate-Palmolive Company, New York, NY (US); Siltech Corporation, Toronto, Ontario (CA)

( * ) Notice: Subject to any disclaimer, the term of this patent is extended or adjusted under 35 U.S.C. 154(b) by 391 days.

(21) Appl. No.: 12/438,368

(22) PCT Filed: Jan. 22, 2009

(86) PCT No.: PCT/US2009/031664
§ 371 (c)(1),
(2), (4) Date: Feb. 23, 2009

(87) PCT Pub. No.: WO2010/085250
PCT Pub. Date: Jul. 29, 2010

(65) Prior Publication Data
US 2011/0027206 A1   Feb. 3, 2011

(51) Int. Cl.
*A61K 8/00* (2006.01)
(52) U.S. Cl. .................................. 424/78.08
(58) Field of Classification Search ........................ None
See application file for complete search history.

(56) References Cited

U.S. PATENT DOCUMENTS

| | | | |
|---|---|---|---|
| 3,389,160 A | 6/1968 | Reid | |
| 4,185,087 A * | 1/1980 | Morlino | 510/122 |
| 4,891,166 A | 1/1990 | Schaefer | |
| 4,895,964 A * | 1/1990 | Margida | 556/425 |
| 5,098,979 A | 3/1992 | O'Lenick | |
| 5,246,607 A | 9/1993 | Schaefer et al. | |
| 5,569,732 A | 10/1996 | Nohr | |
| 6,211,139 B1 | 4/2001 | Keys et al. | |
| 6,242,554 B1 | 6/2001 | Busch et al. | |
| 6,607,717 B1 | 8/2003 | Johnson et al. | |
| 2002/0188058 A1 | 12/2002 | Chaiyawat | |
| 2006/0034792 A1 | 2/2006 | Lazzeri et al. | |
| 2006/0057096 A1 | 3/2006 | Lazzeri et al. | |

FOREIGN PATENT DOCUMENTS

| | | |
|---|---|---|
| EP | 0 017 122 A1 | 10/1980 |
| EP | 535596 A1 | 7/1993 |
| EP | 702686 B1 | 5/2001 |
| GB | 2230787 A | 31/1990 |

OTHER PUBLICATIONS

International Search Report PCT/US2009/031664 mailed Oct. 16, 2009.

\* cited by examiner

*Primary Examiner* — Paul Dickinson
(74) *Attorney, Agent, or Firm* — Michael F. Morgan

(57) ABSTRACT

The present invention is directed to a series of alkyl quaternium silicone compounds having both alkyl groups and fatty quaternary nitrogen groups attached in one molecule, and the intermediates formed during the production thereof, that are suitable for use in personal care and other applications. These compounds by virtue of their unique structure provide outstanding micro-emulsions and provide outstanding hair conditioning. The compounds of the present invention are represented by Formula 1:

Formula 1

$$H_3C-\underset{\underset{CH_3}{|}}{\overset{\overset{CH_3}{|}}{Si}}-[O-\underset{\underset{CH_3}{|}}{\overset{\overset{CH_3}{|}}{Si}}]_a-[O-\underset{\underset{(CH_2)_n}{|}}{\overset{\overset{CH_3}{|}}{Si}}]_b-[O-\underset{\underset{R}{|}}{\overset{\overset{CH_3}{|}}{Si}}]_c-O-\underset{\underset{CH_3}{|}}{\overset{\overset{CH_3}{|}}{Si}}-CH_3$$

with $CH_3$ and $\underset{\underset{CH_3}{|}}{N^+}-Cl^--[(CH_2)_xCH_3]_2$ substituents wherein,
a is an integer ranging from 0 to 200:
b is an integer ranging from 1 to 40:
c is an integer ranging from 1 to 40;
n is an integer ranging from 1 to 50;
x is an integer ranging from 0 to 21; and
R is:

$$-CH_2-CH_2-CH_2-O-\underset{\underset{OH}{|}}{CH}-CH_2-$$

or
R is:

a cyclohexane ring with OH substituent connected to $H_2C-H_2C-$

31 Claims, No Drawings

ALKYL QUATERNIUM SILICONE COMPOUNDS

FIELD OF THE INVENTION

The present invention relates to a series of alkyl quaternium silicone compounds. These compounds are useful in personal care and other application. More specifically, the compounds of the present invention are multifunctional organo-silicone compounds that by virtue of their unique structure, provide outstanding micro-emulsions and hair conditioning.

BACKGROUND OF THE INVENTION

Organo-silicone compounds are one of two types—terminal or internal—depending upon the location of the organofunctional group. Terminal organo-silicone compounds have the organofunctional groups at the alpha and omega termini of the molecule. The basic structure is as follows:

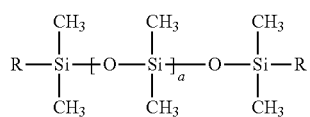

where R is an organofunctional group, and a is an integer representing the degree of polymerization of the molecule.

Internal organo-silicone compounds have the organofunctional groups on non-terminal ends of the molecule, and are also called "comb" or "multifunctional" organo-silicone compounds because the organofunctionality lies in the molecule like the teeth of a comb. These compounds possess the basic structure:

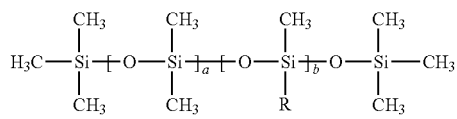

where R is an organofunctional group.

BRIEF SUMMARY OF THE INVENTION

The present invention is directed to multifunctional organo-silicones where two different classes of organofunctional groups are attached to the silicone. It is a surprising and unexpected result of the present invention that when the proper two organofunctional groups in the proper ratio are reacted to make the compounds of the present invention, improvements in the performance of these materials is achieved when applied to personal care products. In some embodiments, this invention relates to a series of alkyl quaternium silicone compounds having both alkyl groups and fatty quaternary nitrogen groups attached in one molecule, and the intermediates formed during the production thereof, that are suitable for use in personal care and other applications. The compounds of the present invention are represented by Formula 1

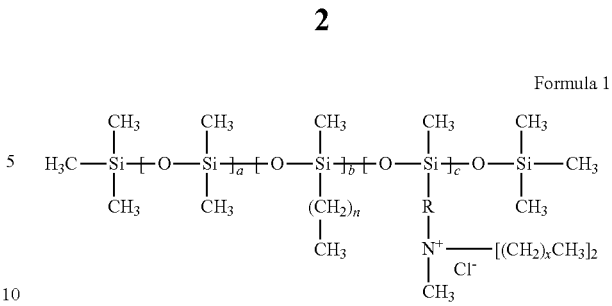

Formula 1 wherein,
a is an integer ranging from 0 to 200;
b is an integer ranging from 1 to 40:
c is an integer ranging from 1 to 40:
n is an integer ranging from 1 to 50:
x is an integer ranging from 0 to 21: and
R is:

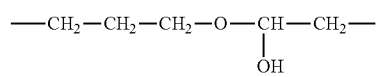

or
R is:

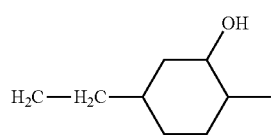

DETAILED DESCRIPTION OF THE INVENTION

This invention relates to a series of alkyl quaternium silicone compounds having both alkyl groups and fatty quaternary nitrogen groups attached in one molecule, and the intermediates formed during the production thereof, that are suitable for use in personal care and other applications. The compounds of the present invention are represented by Formula 1

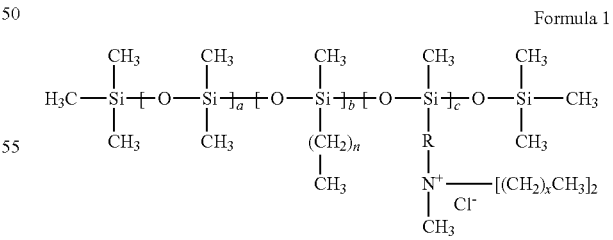

Formula 1 wherein,
a is an integer ranging from 0 to 200;
b is an integer ranging from 1 to 40;
c is an integer ranging from 1 to 40;
n is an integer ranging from 1 to 50;
x is an integer ranging from 0 to 21; and R is:

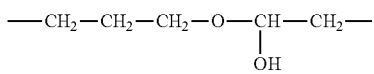

or

R is:

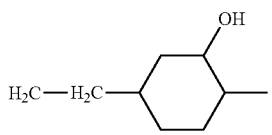

Formula 1 may have a variety of embodiments. In one embodiment of Formula 1, a is 0. In one embodiment of Formula 1, a is 0 and the sum of b and c is 2. In one embodiment, a is 3. In one embodiment, a is 3 and the sum of b and c is 2. In one embodiment, a is 5. In one embodiment, a is 5 and the sum of b and c is 3. In one embodiment, a is 10. In one embodiment, a is 10, and the sum of b and c is 5. In one embodiment, a is 12. In one embodiment, a is 12 and the sum of b and c is 10. In one embodiment, a is 20. In one embodiment, a is 20 and the sum of h and c is 40. In one embodiment of Formula 1, the ratio of a to the sum of b and c is 1:2.

In one embodiment of Formula 1, n is 11. In one embodiment, n is 15. In one embodiment, n is 17. In one embodiment, n is 19. In one embodiment, n is 21. In one embodiment, n is 25.

In one embodiment of Formula 1, x is 11. In one embodiment, x is 15. In one embodiment, x is 17. In one embodiment, x is 19. In one embodiment, x is 21.

Synthesis of Alkyl Quaternium Silicone Compounds

The alkyl quaternium silicone can be prepared using the methods described in U.S. Pat. No. 5,098,979 to O'Lenick, Jr.

Reaction 1

In some embodiments, the alkyl quaternium silicone compounds of the present invention may be prepared by the reaction of:

(a) a silanic hydrogen containing silicone polymer conforming to the following structure:

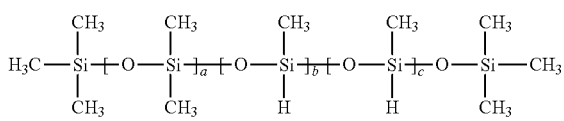

wherein:

a is an integer ranging from 0 to 200:

b is an integer ranging from 1 to 40;

c is an integer ranging from 1 to 40;

with a mixture of:

(b) b moles of an alpha olefin conforming to the following structure:

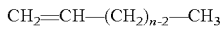

and (c) c moles of a glycidyl epoxy compound conforming to the following structure:

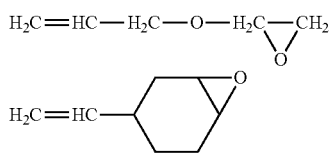

Silanic hydrogen containing silicone polymers suitable for use in the present invention include any polymer conforming to the above-identified structure, wherein a is an integer ranging from 0 to 200; h is an integer ranging from 1 to 40; and c is an integer ranging from 1 to 40. In one embodiment, in a silanic hydrogen containing silicone polymer suitable for use in the present invention, a is 0. In one embodiment, a is 0 and the sum of b and c is 2. In one embodiment, a is 3. In one embodiment, a is 3 and the sum of b and c is 2. In one embodiment, a is 5. In one embodiment, a is 5 and the sum of b and c is 3. In one embodiment, a is 10. In one embodiment, a is 10, and the sum of b and c is 5. In one embodiment, a is 12. In one embodiment, a is 12 and the sum of b and c is 10. In one embodiment, a is 20. In one embodiment, a is 20 and the sum of b and c is 40. In one embodiment, the ratio of a to the sum of b and c is 1:2.

Alpha olefins suitable for use in the present invention include any compound conforming to the above-identified structure, wherein n is an integer ranging from 1 to 50. In one embodiment, n is 11. In one embodiment, n is 15. In one embodiment, n is 17. In one embodiment, n is 19. In one embodiment, n is 21. In one embodiment, n is 25. In some embodiments, the result of Reaction 1 is an intermediate [Intermediate 1], which is one embodiment of the present invention conforming to the following structure:

Intermediate 1

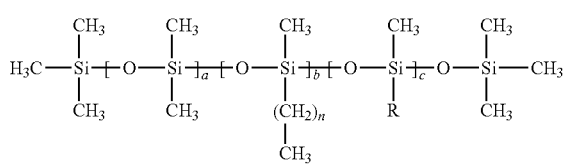

wherein:

a is an integer ranging from 0 to 200;

b is an integer ranging from 1 to 40;

c is an integer ranging from 1 to 40;

n is an integer ranging from 1 to 50; and

R is:

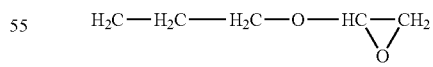

or

R is:

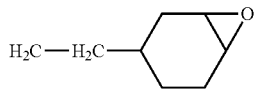

Reaction 2

In some embodiments, the compounds of the present invention may be prepared by the reaction of the above-described Intermediate 1 with "c" moles of diamine:

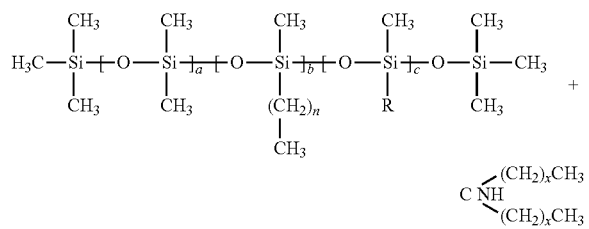

wherein:
a is an integer ranging from 0 to 200;
b is an integer ranging from 1 to 40;
c is an integer ranging from 1 to 40;
n is an integer ranging from 1 to 50;
x is an integer ranging from 0 to 21; and
R is:

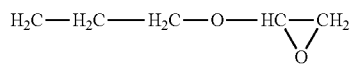

or
R is:

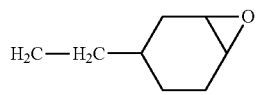

The product of Reaction 2 is the Intermediate 2, which is one embodiment of the present invention and conforms to the following structure:

Intermediate 2

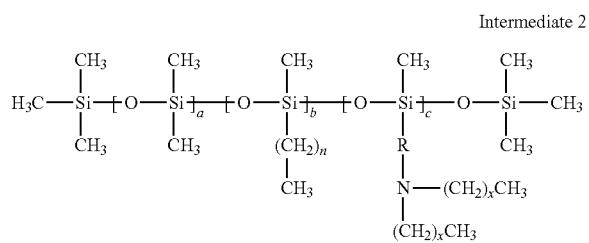

wherein:
a is an integer ranging from 0 to 200;
b is an integer ranging from 1 to 40;
c is an integer ranging from 1 to 40;
n is an integer ranging from 1 to 50;
x is an integer ranging from 0 to 21: and
R is:

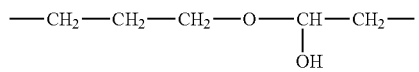

or
R is:

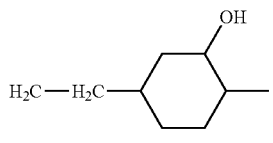

Diamines suitable for use in the present invention include any compound conforming to the above-identified structure, wherein x is an integer ranging from 1 to 21. In one embodiment, diamines suitable for use in the present invention are di-alkyl amines. In one embodiment, x is 11. In one embodiment, x is 15. In one embodiment, x is 17. In one embodiment, x is 19. In one embodiment, x is 21.

Reaction 3

In some embodiments, Intermediate 2 is then quaternized using "c" moles of methyl chloride to yield a Formula 1 compound that is one embodiment of the present invention:

Formula 1

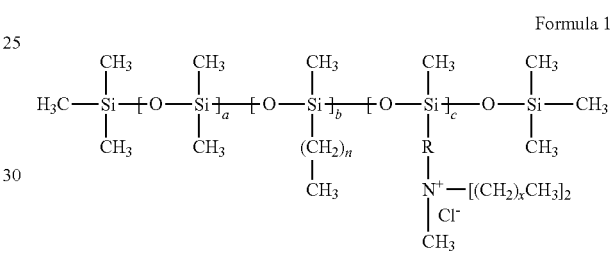

Compositions Including Alkyl Quaternium Silicone Compounds

Compositions including the alkyl quaternium silicone compounds of the present invention exhibit multifunction such as emulsification, active delivery, softening, conditioning, and antistatic properties. The fatty quaternary ammonium functional groups that makes possible certain ionic interactions that are the basis of many useful properties including: increased hydrophilic character, ability to act as a thickener, and ability to aid in the deposition of other materials such as coatings and conditioning agents. The alkyl groups that provide the compounds with its amphiphilic nature allow the silicone backbone to change its orientation in emulsion and on a positively charged surface. In emulsion, the compounds of the present invention will support micellar structure to help emulsify hydrophobic oils. During deposition, the positive charges carried by the fatty quaternary ammonium groups will provide the driving force to bring oil droplets to the surface. Once on the surface, the compounds of the present invention will provide conditioning benefits from both its silicone backbone and hydrophobic functionality. Consequently, due to the presence of both the fatty quaternary ammonium and alkyl functional groups, the compounds of the present invention are useful in many textile and personal care applications requiring softening, conditioning, or antistatic properties. The compounds of the present invention have also been found to exhibit anti-microbial activity.

Hair Care Applications

In some embodiments, the alkyl quaternium silicone compounds of the present invention may result in enhanced softening, conditioning, and/or antistatic benefits. In some embodiments, the alkyl quaternium silicone compounds of the present invention may also provide protective benefits. In some embodiments, a personal care product of the present invention includes a hair care application including, but not limited to: shampoos, hair conditioners, 2-in-1 shampoo/conditioners, hair-rinsing formulations, formulations to aid comb-through of hair, and hair styling aids. In some embodiments, the hair care applications of the present invention include the alkyl quaternium silicone personal care compound of Formula 1, and at least one additive.

In some embodiments, additives suitable for use in the hair care applications of the present invention include, but are not limited to: surfactants, conditioning agents, stabilizers, preservatives, fragrances and color, anti-static agents, and other active ingredients.

Surfactants

In some embodiments, a hair care application of the present invention includes a surfactant. In some embodiments, the surfactant is selected from the group consisting of, but not limited to: anionic surfactants, amphoteric surfactants, nonionic surfactants, zwitterionic surfactants, semi-polar surfactants, and mixtures thereof.

Suitable anionic surfactants include, but are not limited to: the alkyl sulfates, alkyl ether sulfates, alkaryl sulfonates, alkyl sulfosuccinates, n-alkyl sarcosinates. alkyl phosphates, alkyl ether phosphates, alkyl ether carboxylates and alpha-olefin sulfonates, especially their ammonium, sodium, magnesium and mono-, di- and triethanolamine salts. In some embodiments, the alkyl groups generally contain from 8 to 18 carbon atoms and may be saturated or unsaturated. In some embodiments, the alkyl ether sulfates. alkyl ether phosphates and alkyl ether carboxylates may contain from 1 to 10 ethylene oxide units per molecule. In some embodiments, the present invention includes at least one surfactant selected from a particular group of anionic surfactants consisting of: sodium lauryl sulfate. sodium laureth sulfate, ammonium lauryl sulfate. ammonium laureth sulfate, disodium laureth sulfosuccinate: disodium ricinoleamido monoethanolamide ("MEA") sulfosuccinate, sodium cocoyl isethionate. sodium methyl oleoyl taurate, sodium methyl cocoyl taurate, sodium laureth-13 carboxylate, sodium C14-16 olefin sulfonate, sodium laureth-4 phosphate, laureth-3 phosphate, triethylanolamine lauryl sulfate, magnesium lauryl sulfate, sodium tridecyl sulfate, alpha-olefin sulfate, and mixtures thereof. In some embodiments, the present invention includes at least one surfactant selected from a particular group of anionic surfactants consisting of: ammonium laureth sulfate, ammonium lauryl sulfosuccinate, triethanolamine lauryl sulfate, and mixtures thereof. In some embodiments, the present invention includes a sodium lauryl ether sulfate. In some embodiments, the sodium lauryl ether sulfate is selected from the group consisting of: sodium lauryl ether sulfate 1 EO, 2EO, 3EO, and mixtures thereof.

Suitable amphoteric surfactants include, but are not limited to: amides; sultaines; glycinates; glycines; propionates; and mixtures thereof. In some embodiments, pseudo-amphoteric (ampholytic) surfactants such as betaines that are commonly grouped within the designation-amphoteric surfactants may also be used in the present invention. In some embodiments, betaines suitable for use in the present invention include, but are not limited to: cocamidopropyl, coco, oleamidopropyl, and mixtures thereof.

Suitable nonionic surfactants include, but are not limited to: the condensation products of aliphatic (C8-18) primary or secondary linear branched chain alcohols with alkylene oxides or phenols with alkylene oxides, usually ethylene oxide and generally having from 6 to 30 ethylene oxide groups. In some embodiments, nonionic surfactants suitable for use in the compositions of the present invention can include fatty acid alkanolamides. In some embodiments, the fatty acid alkanolamides include those having C10-C18 carbons such as: fatty acid diethanolamides including isostearic acid diethanolamide and coconut fatty acid diethanolamide. In some embodiments, suitable fatty acid monoethanolamides which may be used include coconut fatty acid monoethanolamide and coco mono-isopropanolamide.

Suitable semi-polar surfactants such as amine oxides are also suitable for use in the present invention. In some embodiments, suitable semi-polar surfactants include, but are not limited to: N-alkyl amine oxide; N-stearyl dimethylamine oxide; N-acyl amide oxide; N-cocamidopropyl dimethylamine oxide; and mixtures thereof. In some embodiments, the hydrophobic portion of the amine oxide surfactant may be provided by a fatty hydrocarbon chain having from about 10-21 carbon atoms.

Conditioning Agents

In some embodiments, additional conditioners may be added to the hair application composition in the form of organic cationic conditioning agents for the purpose of providing more hair grooming if deemed necessary. In some embodiments, the additional conditioners are cationic conditioning agents that may include, but are not limited to: homopolymers of dimethyldiallyl ammonium chloride; copolymers of acrylamide and dimethyldiallyl ammonium chloride; homopolymers or copolymers derived from acrylic acid or methacrylic acid which contain cationic nitrogen functional groups attached to the polymer by ester or amide linkages; copolymers of vinylpyrrolidone: acrylic acid esters with quaternary nitrogen functionality; and mixtures thereof. In some embodiments, specific cationic conditioning agents include, but are not limited to: Polyquaterniums 7, 8, 11, 23, and mixtures thereof.

Thickeners

In some embodiments, a hair care application of the present invention includes a thickener. In some embodiments, thickeners can be used to facilitate the application of the shampoo composition to the hair, and are preferably added in sufficient quantities to provide a more luxurious effect. Suitable thickening agents include, but are not limited to: cellulose derivatives; acrylates copolymers: and mixtures thereof. In some embodiments, a hair care application of the present invention includes a nonionic thickener. In some embodiments, suitable nonionic thickeners include, but are not limited to: the condensation products of aliphatic (C8-18) primary or secondary linear or branched chain alcohols or phenols with alkylene oxides; oxyethylcellulose; hydroxypropyl cellulose; starch and starch derivatives such as hydroxyethylamylose and starch amylase; locust bean gum bean; sodium and ammonium chloride; saccharides such as fructose and glucose and derivatives of polysaccharides such as PET-120 methyl glucose dioleate; and mixtures thereof.

Cationic Anti-Static Agents

In some embodiments, a hair care application of the present invention includes a cationic anti-static agent. Suitable cationic anti-static agents include, but are not limited to: cetyl trimethylammonium chloride; cetyl trimethylammonium bromide; stearyltrimethylammonium chloride; primary fatty amines; amine salts: and mixtures thereof. In some embodiments, the alkyl groups of suitable primary fatty amines preferably have from about 12 to 22 carbons atoms and may be substituted or unsubstituted. In some embodiments, suitable amine salts include. but are not limited to: phosphate; citrate lactate; alkyl sulfate salts; and mixtures thereof.

Other Additives

In some embodiments, the hair care applications of the present invention may contain other components in minor amounts (for example less than 1%) commonly found in standard shampoo formulations, including, but not limited to: antibacterial agents; antidandruff agents such as zinc pyridincthione; pearlizing agents; perfumes; dyes and coloring agents: preservatives: viscosity modifiers; proteins; polymers; buffering agents; polyols; moisturizing agents; plant extracts; herb extracts; marine extracts and the like.

The alkyl quaternium silicone compounds may be used in a variety of personal care products including hair care products such as shampoos, hair conditioners, 2-in-1 shampoo/conditioner products, and hair styling aids. Exemplary hair care application compositions are illustrated below.

Shampoo:
Anionic surfactant such as 10-40 weight % sodium lauryl ether sulfate;
A cationic conditioning agent such as 0.5 to 5 weight % Polyquaternium-7;
A stabilizer such as 1-10 weight % behenyl alcohol dispersion;
Preservative such as 0.05-0.8 weight % tetrasodium EDTA or 0.05-0.4 weight % preservative such as DMDM hydantoin:
0-2 weight % of a fragrance;
0.1 to 5 weight % of an alkyl quaternium silicone of Formula 1; and
QS water (especially deionized).

Shampoo formulations may be prepared using the alkyl quaternium silicone compounds of Example 1 (Formula 1). Exemplary shampoo formulations are shown in Table A.

TABLE A

Shampoo formula using aliphatic cationic silicone compositions

| | (%) | | |
|---|---|---|---|
| Ingredient | A | B | C |
| Deionized water and minors | q.s. to 100 | q.s. to 100 | q.s. to 100 |
| Sodium Lauryl Ether Sulfate (70%) | 10 | 10 | 10 |
| Polyquat-7 | 3.5 | 3.5 | 3.5 |
| Behenyl alcohol | 8 | 8 | 8 |
| Ethylene Glycol Distearate | 0.2 | 0.2 | 0.2 |
| Coconut diethanolamide | 2 | 2 | 2 |
| Formula 1 silicone | 0.5 | 1 | 2 |

Anti-Dandruff Shampoo:
Anionic Surfactant such as 10-40 weight % sodium lauryl ether sulfate;
A cationic conditioning agent such as 0.5 to 5 weight % Polyquaternium-7;
A stabilizer such as 1-10 weight % behenyl alcohol dispersion;
Preservative such as 0.05-0.8 weight % tetrasodium EDTA or 0.05-0.4 weight % preservative such as DMDM hydantoin;
Fungicide such as 0.1 to 0.8 weight % Climbazole;
0-2 weight % of a fragrance;
0.1 to 5 weight % of an alkyl quaternium silicone of Formula 1; and
QS water (especially deionized).

Anti-dandruff shampoo formulations may be prepared using the alkyl quaternium silicone compounds of Example 1 (Formula 1). Exemplary anti-dandruff shampoo formulations are shown in Table B.

TABLE B

Anti-Dandruff Shampoo formula using aliphatic cationic silicone compositions

| | (%) | | |
|---|---|---|---|
| Ingredient | A | B | C |
| Deinoized Water and minors | q.s. to 100 | q.s. to 100 | q.s. to 100 |
| Sodium Lauryl Ether Sulfate (70%) | 10 | 10 | 10 |
| Polyquat-7 | 3.5 | 3.5 | 3.5 |
| Behenyl alcohol | 8 | 8 | 8 |
| Ethylene Glycol Distearate | 0.2 | 0.2 | 0.2 |
| Coconut diethanolamide | 2 | 2 | 2 |
| Climbazole | 0.4 | 0.4 | 0.4 |
| Silicone of formula 1 | 0.5 | 1 | 2 |

Rinse Off Hair Conditioner:
A water soluble quaternary ammonium salt such as 0.20-2 weight % cetyl trimethyl ammonium chloride;
Thickener such as 0.5 to 5 weight % cetearyl alcohol a mixture of stearyl alcohol and cetyl alcohol;
Preservatives such as Germall 115. methyl paraben and propyl paraben;
Thickener such as 0.1 to 1 weight % glyceryl monostearate;
0.25 to 2 weight % Mineral oil;
0 to 1 weight % of a fragrance;
0.1 to 5 weight % of an alkyl quaternium silicone of Formula 1; and
QS Water (especially deionized).

Rinse off hair conditioners may be prepared using the alkyl quaternium silicone compounds of Example 1 (Formula 1). Exemplary formulations for the rinse off conditioners are shown in Table C.

TABLE C

Rinse-off hair conditioner formulas using aliphatic cationic silicone compositions

| | (%) | | |
|---|---|---|---|
| Ingredient | A | B | C |
| Dionized water and minors | q.s. to 100 | q.s. to 100 | q.s. to 100 |
| Cetrimonium Chloride (CTAC) | 0.5 | 0.5 | 0.5 |
| Glyceryl Monostearate | 0.25 | 0.25 | 0.25 |
| Cetearyl Alcohol | 5 | 5 | 5 |
| Formula 1 Silicone | 0.5 | 1 | 2 |

Leave-On Hair Conditioner:
A water soluble quaternary ammonium salt such as 0.20-2 weight % cetyl trimethyl ammonium chloride:
Thickener such as 0.5 to 5 weight % cetearyl alcohol a mixture of stearyl alcohol and cetyl alcohol;
Preservatives such as Germall 115, methyl paraben and propyl paraben;
Thickener such as 0.1 to 1 weight % glyceryl monostearate;
Alkyl benzoate such as 0.5 to 5 weight % $C_{12}$ to $C_{15}$ alkyl benzoate:
0.25 to 2 weight % Mineral oil:
0 to 1 weight % of a fragrance;
to 5 weight % of an alkyl quaternium silicone of Formula 1;
QS Water (especially deionized).

Leave on hair conditioner formulations may be prepared using the alkyl quaternium silicone compounds of Example 1

(Formula 1). Exemplary formulations for the leave on hair conditioners are shown in Table D.

TABLE D

Leave-on hair conditioner formulas using aliphatic cationic silicone compositions

| Ingredient | (%) | | |
|---|---|---|---|
| | A | B | C |
| Deinonized water and minors | q.s. to 100 | q.s. to 100 | q.s. to 100 |
| Cetrimonium Chloride | 0.25 | 0.25 | 0.25 |
| Glyceryl Monostearate | 0.125 | 0.125 | 0.125 |
| Cetearyl Alcohol | 1.5 | 1.5 | 1.5 |
| C12-15 alkyl benzoate | 2 | 2 | 2 |
| Formula 1 Silicone | 0.5 | 1 | 2 |

Body Wash:
Anionic surfactant such as 25 to 40 weight % sodium pareth sulfate;
Nonionic surfactant such as 5 to 15 weight % cocoamidopropyl betaine;
Cationic polymer including 0.3 to 3 weight % Polyquaterium 7:
Alkyl polysaccharides surfactant such as 0.3 to 3 weight % decyl glucose;
Preservatives such as 0.05-0.8 weight % tetrasodium EDTA or 0.05-0.5 weight % preservative such as DMDM hydantoin;
to 0.15 weight percent citric acid:
0 to 1 weight % of a fragrance;
to 5 weight % of an alkyl quaternium silicone of Formula 1; and
QS Water (especially deionized).

Body wash formulations may be prepared using the alkyl quaternium silicone compounds of Example 1 (Formula 1). Exemplary formulations for body washes are shown in Table E.

TABLE E

Body Wash formula using aliphatic cationic silicone compositions

| Ingredient | (%) | | |
|---|---|---|---|
| | A | B | C |
| Demineralized Water and minors | q.s. to 100 | q.s. to 100 | q.s. to 100 |
| SO3Na Pareth Sulfate Base - 25.5% | 32.2 | 32.2 | 32.2 |
| Cocoamidopropyl Betaine | 10 | 10 | 10 |
| Polyquaternium-7 | 2.5 | 2.5 | 2.5 |
| Decyl Glucoside | 2.25 | 2.25 | 2.25 |
| Sodium Chloride | 1 | 1 | 1 |
| Silicone of formula 1 | 0.5 | 1 | 2 |

Liquid Hand Soap:
30 to 45 weight % of sodium salt of an ethoxylated pareth sulfate surfactant having 1 to 3 moles of ethylene oxide;
0.7 to 7 weight % of a nonionic surfactant such as cocamidopropyl betain;
Preservatives such as 0.05-0.8 weight % tetrasodium EDTA or 0.05-0.5 weight % preservative such as DMDM hydantoin;
to 2 weight % of a fragrance; and
to 3 weight % of an alkyl quaternium silicone of Formula 1.

Liquid Hand Soap formulations may be prepared using the alkyl quaternium silicone compounds of Example 1 (Formula 1). Exemplary formulations for the liquid hand soap are shown in Table F.

TABLE F

Liquid Hand Soap formula using aliphatic cationic silicone compositions

| Ingredient | (%) | | |
|---|---|---|---|
| | A | B | C |
| Demineralized water and minors | q.s. to 100 | q.s. to 100 | q.s. to 100 |
| SO3Na Pareth 145- 2EO Sulfate Base - 25.5% | 37.1 | 37.1 | 37.1 |
| Carbopol ™ Aqua S-1 Polymer (B F GOODRICH) | 8.95 | 8.95 | 8.95 |
| Cocoamidopropyl Betaine | 5.64 | 5.64 | 5.64 |
| Silicone of formula 1 | 0.5 | 1 | 2 |

The alkyl quaternium silicone compounds of the present invention may also be used in personal care compositions such as deodorants and/or antiperspirants. Representative ingredients of deodorants and/or antiperspirants are found in U.S. Patent Application Publication No. 2004/0062738: U.S. Pat. Nos. 7,105,691; and 6,969,510, all of which are assigned to Colgate-Palmolive Co.

Home Care Applications

The alkyl quaternium silicone compounds may also be used in home care compositions such as dish liquid, fabric softener, hard surface cleaner light duty liquid detergents, and detergent. In dishwashing liquids, the alkyl quaternium silicone compositions may allow for use of stronger surfactants which typically irritate the skin. An example of a light duty liquid soap is as follows. For light duty liquid compositions, representative ingredients are described in: U.S. Pat. No. 6,509,306, assigned to Colgate-Palmolive Co.

Light Duty Liquid Soap:
15 to 30 weight % of a sodium salt of a $C_8$-$C_{16}$ linear alkyl benzene sulfonate surfactant;
5 to 15 weight % of an ammonium or sodium salt of an ethoxylated $C_8$-$C_{18}$ alkyl ether sulfate surfactant having 1 to 3 moles of ethylene oxide;
5 to 15 weight % of an ammonium or sodium salt of a $C_8$-$C_{18}$ alkyl sulfate surfactant;
0.6 to 6 weight % of an nonionic surfactant including $C_{12}$-$C_{14}$ betaine or $C_{12}$-$C_{14}$ amine oxide;
Preservatives such as 0.05-0.5 weight % preservative such as DMDM hydantoin;
0 to 1 weight % of a fragrance;
to 3 weight % of an alkyl quaternium silicone of Formula 1; and
Solubilizing agents such as 0.3 to 3 weight % sodium xylene sulfonate.

Exemplary light duty liquid formulations are shown in Table G.

TABLE G

Light Duty Liquid formula using aliphatic cationic silicone compositions

| Ingredient | (%) | | |
|---|---|---|---|
| | A | B | C |
| C8-C16 Linear Alkyl benzene sulfonate - Mg salt | 22 | 22 | 22 |

TABLE G-continued

Light Duty Liquid formula using aliphatic cationic silicone compositions

| Ingredient | (%) | | |
|---|---|---|---|
| | A | B | C |
| C8-C18 ethoxylated alkyl ether sulfate - 1.3EO) (NH$_4$ or Na salt) | 9 | 9 | — |
| C8-C18 alkyl sulfate (NH$_4$ or Na salt) | — | 10 | 9 |
| C12/C14 Betaine | — | 5 | — |
| C12/C14 Amine Oxide | 5 | — | 4 |
| Sodium Chloride | 0.4 | 0.4 | 0.4 |
| Pentasodium Pentetate | 0.125 | 0.125 | 0.125 |
| Sodium Xylene Sulfonate | 2 | 2 | 2 |
| Silicone of formula 1 | 1 | 1 | 2 |

EXAMPLES

The invention is further described in the following examples. The examples are merely illustrative and do not in any way limit the scope of the invention as described and claimed.

Preparation of Products of the Present Invention

The following examples illustrate an exemplary method to prepare the products of the present invention using the following reactants: silanic hydrogen compounds; alpha olefins, glycidyl epoxides; quaternization compound such as methyl chloride; and diamines.

Silanic Hydrogen Compounds

Silanic hydrogen compounds conforming to the following structure below are commercially available from Siltech Corporation:

$$H_3C-\underset{\underset{CH_3}{|}}{\overset{\overset{CH_3}{|}}{Si}}-\left[O-\underset{\underset{CH_3}{|}}{\overset{\overset{CH_3}{|}}{Si}}\right]_a-\left[O-\underset{\underset{H}{|}}{\overset{\overset{CH_3}{|}}{Si}}\right]_b-\left[O-\underset{\underset{H}{|}}{\overset{\overset{CH_3}{|}}{Si}}\right]_c-O-\underset{\underset{CH_3}{|}}{\overset{\overset{CH_3}{|}}{Si}}-CH_3$$

wherein:
a is an integer ranging from 0 to 200;
b is an integer ranging from 1 to 40;
c is an integer ranging from 1 to 40.

The specific values reported below for the molecule were determined by Si-29 nmr:

TABLE 1

| Silanic Hydrogen Compounds | | |
|---|---|---|
| Example | a | b + c |
| 1 | 0 | 2 |
| 2 | 3 | 2 |
| 3 | 5 | 3 |
| 4 | 10 | 5 |
| 5 | 12 | 10 |
| 6 | 20 | 40 |

Olefinic Compounds

Alpha olefins conforming to the following structure below are commercially available from a variety of sources including Chevron: $CH_2=CH-(CH_2)_{n-2}-CH_3$.

TABLE 2

| Alpha Olefin Compounds | |
|---|---|
| Example | n |
| 7 | 11 |
| 8 | 15 |
| 9 | 17 |
| 10 | 19 |
| 11 | 21 |
| 12 | 25 |

Example 13

Glycidyl Epoxide

Glycidyl epoxide is an item of commerce conforming to the following structure below that is commercially available from Ciba:

$$H_2C=HC-H_2C-O-H_2C-CH_2 \quad \text{or}$$
$$\underset{}{\overset{}{\phantom{X}}}\overset{}{O}$$

$$H_2C=HC-\text{(cyclohexyl)}-O$$

Example 14

Methyl Chloride

Methyl chloride conforming to the following structure below is commercially available from Air Gas: $CH_3Cl$ Diamines Diamines conforming to the following structure below are commercially available from Akzo Nobel: $H-N-[(CH_2)_x CH_3]_2$ wherein x is an integer ranging from 1 to 21.

TABLE 3

| Diamines | |
|---|---|
| Example | x |
| 15 | 11 |
| 16 | 15 |
| 17 | 17 |
| 18 | 19 |
| 20 | 21 |

Products of the Present Invention

Intermediate 1

General Procedure: The specified number of grams of alpha olefin (Examples 7-12) and the specified number of grams of glycidyl epoxide (Example 13) are added to a vessel having agitation and cooling. Next the specified number of grams of silanic hydrogen (Examples 1-6) is added. The batch is then heated to 80° C. Next 10 ppm of platinum catalyst (based upon the weight of all materials to be added) is added. Cooling is added to control the exotherm. It is not uncommon for the temperature to rise from 80° C. to 120° C. Hold at 120° C. for 4 hours, checking the Silanic hydrogen content until it becomes vanishing small.

TABLE 4

Intermediate 1 Compounds

| Example | Silanic Hydrogen (grams) | Alpha Olefin (grams) | Glycidyl Epoxide (grams) |
|---|---|---|---|
| 21 | 1322.7 | 1542.9 | 134.1 |
| 22 | 1443.6 | 1263.0 | 293.1 |
| 23 | 1653.9 | 741.9 | 604.2 |
| 24 | 1826.6 | 409.6 | 963.8 |
| 25 | 1684.2 | 783.9 | 691.6 |
| 26 | 1197.3 | 567.9 | 500.9 |
| 27 | 1826.6 | 409.6 | 968.8 (cyclic epoxide) |
| 28 | 1443.6 | 1263.0 | 293.1 (cyclic epoxide) |

Intermediate 2

Amination Reaction: The specified number of grams of Intermediate 1 (Examples 21-26) are added to a vessel having agitation and cooling. Next the specified number of grams of anhydrous ethanol is added, following by the specified number of grams of diamine (Examples 15-20). The batch is then heated to 80° C. until all of the amine has been converted from secondary amine to tertiary amine.

TABLE 5

Intermediate 2 Compounds

| Example | Intermediate 1 (grams) | Diamine (grams) | Ethanol (grams) |
|---|---|---|---|
| 29 | 3186.6 | 89.8 | 655.3 |
| 30 | 3100.0 | 166.9 | 653.4 |
| 31 | 2705.2 | 325.8 | 606.2 |
| 32 | 2702.7 | 458.0 | 632.1 |
| 33 | 2900.0 | 370.4 | 654.0 |
| 34 | 2100.0 | 261.0 | 472.2 |
| 35 | 2702.7 | 458.0 | 632.1 |
| 36 | 3100.0 | 166.9 | 653.4 |

Alkyl Quaternium Silicone Compounds

Quaternization: The specified number of grams of Intermediate 2 (Examples 27-32) is added to a vessel with mixing. The specified number of grams of methyl chloride (Example 14) is then added to yield Formula 1 of the present invention.

TABLE 6

Multifunctional Organo-Silicone Compounds

| Example | Intermediate 2 (grams) | Methyl Chloride (grams) |
|---|---|---|
| 33 | 3088.3 | 43.1 |
| 34 | 3083.2 | 99.9 |
| 35 | 2788.1 | 192.5 |
| 36 | 2884.4 | 272.4 |
| 37 | 3058.0 | 219.5 |
| 38 | 2143.0 | 161.3 |
| 39 | 2884.4 | 272.4 |
| 40 | 3083.2 | 99.9 |

Example 41

The following molecules were used in the conditioner composition described below for comparative testing. The test methods used are reported below.

$$\begin{array}{c} CH_3 \\ | \\ -[Si-O]_x-[Si-O]_m-[Si-O]_n- \\ | \\ CH_3 \end{array} \quad \begin{array}{c} CH_3 \\ | \\ | \\ CH_2 \end{array} \quad \begin{array}{c} C_{18} \\ | \\ | \\ CH_3 \end{array}$$

with side chain:
$CH_2$–$CH_2$–O–$CH_2CHCH_2$–$\overset{+}{N}(C_2H_5)(CH_3)(C_2H_5)$ with OH

| Sample | x | m | n |
|---|---|---|---|
| Control 1 (dimethicone 2000 cst.) | — | 0 | 0 |
| Inventive J2-818A | 20 | 2 | 8 |
| Inventive J2-618A | 20 | 4 | 6 |
| Inventive J2-418-A | 20 | 6 | 4 |
| Inventive J2-218A | 20 | 8 | 2 |
| Inventive T2-818A | 40 | 12 | 8 |
| Inventive 2N-1618A | 80 | 24 | 16 |
| Control 2 (J2) | 20 | 10 | 0 |

| Ingredient | Weight % |
|---|---|
| Water | Q.S. to 100 |
| Cetrimonium Chloride (CTAC) | 0.5 |
| Cetyl alcohol | 2 |
| Stearyl alcohol | 3 |
| Glyceryl monostearate | 0.25 |
| Preservatives and fragrance | 0.52 |
| Alkyl quaternium silicone polymer | 0.5 |

Batches are made in a 1-kg sized kettle on an IKA (Eurostar Power Control-Vis) mixer while on agitation at 150 rpm using a stainless steel blade. First, heat the water-phase to 85° C. In the meantime, weigh out the oil-phase, allow it to melt until this phase also reached 85° C. When the water-phase was at 85° C., deposit the melted oil-phase into the same and allowed them to emulsify at a higher speed (250 rpm) for 20 minutes. The batch is then air-cooled to room temperature with an average cooling rate of about 1° C./min. At 65° C., add the silicone. Then the batch is further cooled down till its temperature is 38° C., then add the fragrance and preservatives. At room temperature (25° C.). adjust the pH using citric acid to reduces the pH to the acidic side of 3.6-4.4.

A set a panelists evaluated the wet and dry combing of J2-818A, J2-218A, and Control 1. The panelist ratings were averaged together and are reported below.

| Sample | Wet Combing | Dry Combing |
|---|---|---|
| J2-818A | 7.604 | 7.667 |
| J2-218A | 7.042 | 7.69 |
| Control 1 | 6.563 | 7.262 |

A set a panelists evaluated the wet and dry combing of J2-818A, J2-618A, and Control 2. The panelist ratings were averaged together and are reported below.

| Sample | Wet Combing | Dry Combing |
|---|---|---|
| J2-818A | 7.57 | 8.286 |
| J2-618A | 7.167 | 8.38 |
| Control 2 | 6.381 | 7.69 |

A third set of panelists evaluated hair softness along with instrument analysis using a Texture Analyzer 3-point bending test comparing Control 2 to J2-818A. The results are listed below. The alkyl quaternium silicone provided softer hair according to the tests.

|  | Panel Evaluation | Texture Analyzer 3 point bend Force (kg) |
| --- | --- | --- |
| J2-818A | 56 | 0.1605 |
| Control 2 | 91 | 0.211 |

The ability of the alkyl quaternium silicone to increase deposition of materials from the conditioner composition were tested. The material tested was Ceraphyl™ RMT castor oil maleate from ISP Corp. The comparative compositions were prepared as shown below.

| Ingredient | Weight % | Weight % | Weight % |
| --- | --- | --- | --- |
| Water | Q.S. to 100 | Q.S. to 100 | Q.S. to 100 |
| Cetrimonium Chloride (CTAC) | 0.5 | 0.5 | 0.5 |
| Cetyl alcohol | 2 | 2 | 2 |
| Stearyl alcohol | 3 | 3 | 3 |
| Glyceryl monostearate | 0.25 | 0.25 | 0.25 |
| Preservatives and fragrance | 0.52 | 0.52 | 0.52 |
| Ceraphyl ™ RMT castor oil maleate | 0.5 | 0.5 | 0.5 |
| J2-818A | 0.5 | — | — |
| Dimethicone (2000 cst.) | — | 0.5 | — |

The compositions were tested for deposition. The results are shown below. As can be seen, the inventive alkyl quaternium silicone polymer increases the deposition of the castor oil maleate.

| Sample | Deposition of Ceraphyl ™ RMT (ppm) |
| --- | --- |
| J2-818A | 4.421 |
| Control 1 with dimethicone | 1.308 |
| Sample with no J2-218A or dimethicone | 1.467 |

A set a panelists evaluated the wet and dry combing of T2-818A and J2-818A on hair after washing using the conditioner composition above. The panelist ratings were averaged together and are reported below.

| Sample | Wet Combing | Dry Combing |
| --- | --- | --- |
| T2-818A | 7.5 | 7.6 |
| J2-818A | 6.8 | 7.5 |

A set a panelists evaluated the wet and dry combing of 2N-1618A and T2-818A on hair after washing using the conditioner composition above. The panelist ratings were averaged together and are reported below.

| Sample | Wet Combing | Dry Combing |
| --- | --- | --- |
| 2N-1618A | 8.262 | 8.119 |
| T2-818A | 6.429 | 7.024 |

Test Methods

Preparation of Hair Tresses 2.5 g of slightly damaged Caucasian hair is used to make one hair tress. The tress is pre-washed with sodium lauryl sulfate (SLS) solution twice to remove residues, and air dried overnight. During application, hair tresses are pre-wetted, and 0.5 g of product to test is evenly applied on using a syringe. The product is rubbed in for 1 minute and then rinsed under water for 30 seconds. The tress is used either wet or allowed to dry.

Wet and Dry Combing

Eight trained panelists are used to comb through tresses and give evaluation on both ranking and rating under both wet and dry conditions. Three replicates are used for a comb test. All the tresses are evaluated on a 1 to 9 scale, with 9 being the easiest to comb.

Hair Softness

Six hair tresses are made to evaluate two conditioner prototypes, with three for the inventive silicone and three for the control. The panelists are first asked to wash their hands with anti-bacterial soap and then wipe them dry using alcohol swabs. Then, the wiped hands should be allowed to air dry for a few minutes until completely dry. Panelists then evaluate the softness of the hair by feeling with their finger tips the mid-third of the hair for softness. They are asked to rate the 6 tresses on the scale of 1-6, where 1 is the softest and 6 the coarsest. Eight trained panelists are used. The numbers reported for each composition are the sum of the rating for each of the three tresses for all eight panelists. To obtain the average rating, the sum can be divided by 24.

Texture Analyzer

As an initial step, force calibration is performed using the 2000 g weight provided, which is followed by setting the parameters. The main parameters used are: Test Mode: Compression, Test Speed: 1.00 mm/sec, Post-Test Speed: 10 mm/sec, Target Mode: Distance, Distance: 13.000 mm and Trigger Force: 5.0 g. A macro program is used to record the data and measure the key parameters, in this case, the peak force and the total work required to bend the hair. A three-point-bending system is utilized to measure the hair softness. The setup is comprised of a three-point-bending rig that has a base, two adjustable supports and an arm with the attached third blade that approaches to between the two adjustable supports. The hair tress is laid along the supports in such a way that the top end of the tress is placed at the edge of the T.A. platform. When the test is started, the T.A. arm moves down the specified distance of 13.000 mm, bends the hair tress and then springs back up. While the test is being run, the data is recorded as a graph (force profile), and the desired data specified in the macro, area under the graph and the maximum (peak) force required to bend the hair, are recorded in a spreadsheet. The maximum force is a measure of the softness of the hair. The softer the hair. the lesser the force required to bend the hair. For enhanced accuracy, triplicate tresses (three tresses treated in the same way using the same test product) are measured in the test, and each hair sample is run five times to get the average reading. The weight of the tresses is also measured and used to normalize the T.A. values to eliminate any error from the weight difference between hair tresses. An ANOVA test is then performed to obtain statistical information.

Deposition

Hair tresses are first treated with the conditioner test product using the standard comb-test procedure for treating tresses (described above), then soaked in a 0.5 l(16 oz.) jar with 100 ml Hexane for 30 minutes. After half-an-hour soaking, containers are shaken for three minutes before the Hexane solution is collected and condensed for evaluation by HPLC-MS. Six replicates for each are conducted and averaged together. An ANOVA test is conducted to determine the statistical significance.

What is claimed is:

1. An alkyl quaternium silicone compound of Formula 1:

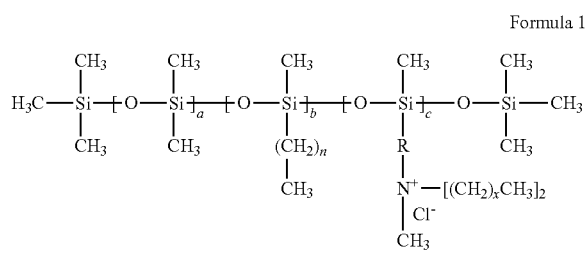

Formula 1 wherein,
a is an integer ranging from 0 to 200;
b is an integer ranging from 1 to 40;
c is an integer ranging from 1 to 40;
n is an integer ranging from 1 to 50;
x is an integer ranging from 0 to 21; and
R is:

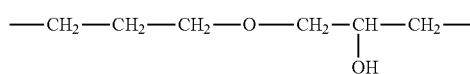

or
R is:

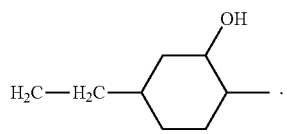

2. The compound of claim 1, wherein a ratio of a to the sum of b and c is 2:1.
3. The compound of claim 1, wherein n is 11.
4. The compound of claim 1, wherein n is 15.
5. The compound of claim 1, wherein n is 17.
6. The compound of claim 1, wherein n is 19.
7. The compound of claim 1, wherein n is 21.
8. The compound of claim 1, wherein n is 25.
9. The compound of claim 1, wherein x is 11.
10. The compound of claim 1, wherein x is 15.
11. The compound of claim 1, wherein x is 17.
12. The compound of claim 1, wherein x is 19.
13. The compound of claim 1, wherein x is 21.
14. The compound of claim 1, wherein a is 40, b is 8, and c is 12.
15. The compound of claim 14, wherein n is 17.
16. The compound of claim 1, wherein a is 20 and the sum of b and c is 10.
17. The compound of claim 16, wherein b is 2 and c is 8.
18. The compound of claim 16, wherein b is 4 and c is 6.
19. The compound of claim 16, wherein b is 6 and c is 4.
20. The compound of claim 16, wherein b is 8 and c is 2.
21. The compound of claim 17, wherein n is 17.
22. The compound of claim 18, wherein n is 17.
23. The compound of claim 19, wherein n is 17.
24. The compound of claim 20, wherein n is 17.
25. The compound of claim 1, wherein a is 80 and the sum of b and c is 40.
26. The compound of claim 25, wherein b is 16 and c is 24.
27. The compound of claim 26, wherein n is 17.
28. A personal care composition comprising the alkyl quaternium silicone compound of claim 1 and at least one material chosen from a surfactant and a conditioning agent.
29. A home care composition comprising the alkyl quaternium silicone compound of claim 1 and a surfactant.
30. An organo-silicone compound of Intermediate 1:

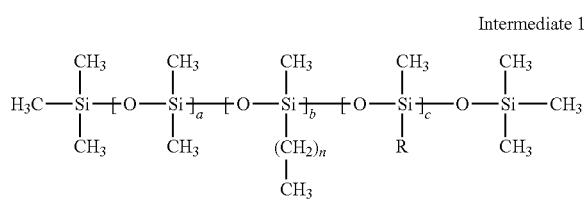

Intermediate 1 wherein:
a is an integer ranging from 0 to 200;
b is an integer ranging from 1 to 40;
c is an integer ranging from 1 to 40;
n is an integer ranging from 1 to 50; and
R is:

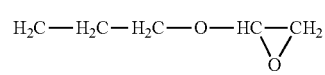

or
R is:

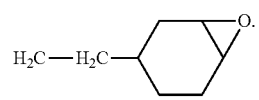

31. An organo-silicone compound of Intermediate 2:

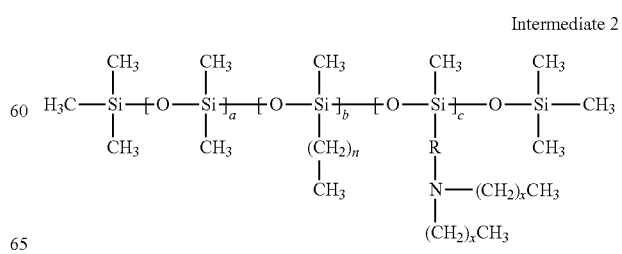

Intermediate 2 wherein:
a is an integer ranging from 0 to 200;
b is an integer ranging from 1 to 40;
c is an integer ranging from 1 to 40;
n is an integer ranging from 1 to 50;
x is an integer ranging from 0 to 21; and
R is:
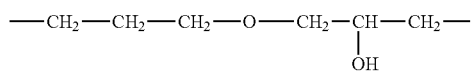
or
R is:
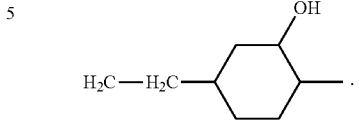
* * * * *